US012599470B2

(12) United States Patent (10) Patent No.: US 12,599,470 B2
Chen (45) Date of Patent: Apr. 14, 2026

(54) SURGICAL-USE MEDICAL APPARATUS AND SYSTEM THEREFOR

(71) Applicant: COHORIZON INTELLECTUAL PROPERTY INC., Beijing (CN)

(72) Inventor: Chieh Hsiao Chen, Taichung City (TW)

( * ) Notice: Subject to any disclaimer, the term of this patent is extended or adjusted under 35 U.S.C. 154(b) by 886 days.

(21) Appl. No.: 17/909,329

(22) PCT Filed: Mar. 8, 2021

(86) PCT No.: PCT/CN2021/079593
§ 371 (c)(1),
(2) Date: Sep. 2, 2022

(87) PCT Pub. No.: WO2021/180044
PCT Pub. Date: Sep. 16, 2021

(65) Prior Publication Data
US 2023/0083110 A1 Mar. 16, 2023

Related U.S. Application Data

(60) Provisional application No. 62/986,808, filed on Mar. 9, 2020.

(51) Int. Cl.
*A61F 2/04* (2013.01)

(52) U.S. Cl.
CPC ...... *A61F 2/042* (2013.01); *A61F 2220/0008* (2013.01); *A61F 2230/0091* (2013.01)

(58) Field of Classification Search
CPC .............. A61F 2/042; A61F 2220/0008; A61F 2230/0091; A61F 2/0022; A61F 2002/047; A61F 2230/001; A61F 2/04; A61B 2017/32096; A61B 2090/034
See application file for complete search history.

(56) References Cited

U.S. PATENT DOCUMENTS 5,514,176 A * 5/1996 Bosley, Jr. ................ A61F 2/88
606/191
10,722,392 B2 7/2020 Pung et al.
2003/0069647 A1 4/2003 Desmond, III et al.
2005/0055076 A1 3/2005 Huxel et al.
(Continued)

FOREIGN PATENT DOCUMENTS

CN 106102655 B 11/2018
CN 208864415 U 5/2019
(Continued)

OTHER PUBLICATIONS

The International Search Report and Written Opinion dated Jun. 4, 2021 from the International Application PCT/CN2021/079593.

*Primary Examiner* — Suzette J Gherbi
(74) *Attorney, Agent, or Firm* — Haverstock & Owens, A Law Corporation

(57) ABSTRACT
A surgical medical device includes a rod portion and a support portion extending from the rod portion. The support portion has a first stretch segment, a second stretch segment, and a third stretch segment disposed between the first stretch segment and the second stretch segment. The surgical medical device has a control mechanism. The surgical medical device stretches or contracts the first stretch segment, the third stretch segment and the second stretch segment by the control mechanism.

21 Claims, 15 Drawing Sheets

(56)                    References Cited

U.S. PATENT DOCUMENTS

| 2017/0000598 | A1 |   | 1/2017 | Bachar |
| 2018/0319114 | A1 |   | 11/2018 | Huang et al. |
| 2019/0038443 | A1 | * | 2/2019 | Sicotte .................... A61F 2/885 |
| 2021/0059704 | A1 |   | 3/2021 | Kilemnik |

FOREIGN PATENT DOCUMENTS

| CN |   | 110072473 | A |   | 7/2019 |   |
| CN |   | 110799237 | A |   | 2/2020 |   |
| CN |   | 109414315 | B |   | 8/2021 |   |
| WO | WO-2017184887 | A1 | * | 10/2017 | .......... A61F 2/9517 |
| WO |   | 2019180711 | A1 |   | 9/2019 |   |

* cited by examiner

900

1100

1114A

1112

1110

1114B

SURGICAL-USE MEDICAL APPARATUS AND SYSTEM THEREFOR

BACKGROUND OF THE INVENTION

Field of the Invention

The present disclosure relates to a surgical medical device and system and, more particularly, to a surgical medical device and system for use in prostate surgery or bladder neck incision.

Description of the Prior Art

Conventional medical devices are used in prostate surgery or bladder neck incision performed on patients with prostate enlargement. However, their presence, typically lasting several days in duration, in the prostate poses a risk: the conventional medical device either slides and falls into the bladder, or slides to the sphincter to cause relaxation thereof. (Bladder sphincter relaxation has a sequela, such as leaking urine.) In view of this, it is necessary to provide a surgical medical device and system effective in precluding the aforesaid risk: the conventional medical device placed in the prostate either slides and falls into the bladder, or slides to the sphincter to cause relaxation thereof.

SUMMARY OF THE INVENTION

In view of the aforesaid drawbacks of the prior art, it is an objective of the disclosure to provide a surgical medical device and system effective in preventing a loose sphincter typical of conventional medical devices which are likely to slide and fall into the bladder or slide to the sphincter.

In order to achieve the above and other objectives, the disclosure provides a surgical medical device, comprising: a support portion having a first stretch segment, a second stretch segment, and a third stretch segment disposed between the first stretch segment and the second stretch segment, wherein the surgical medical device has a control mechanism, and the surgical medical device stretches or contracts the first stretch segment, the third stretch segment and the second stretch segment by the control mechanism.

In a preferred embodiment of the disclosure, the support portion has at least one arcuate end at the first stretch segment.

In a preferred embodiment of the disclosure, the support portion has at least one folding auxiliary portion at the second stretch segment.

In a preferred embodiment of the disclosure, the support portion comprises a plurality of support conducting wires.

In a preferred embodiment of the disclosure, the support portion is made of a memory alloy, and the control mechanism is in a plastic state when the first stretch segment, the third stretch segment and the second stretch segment are below a first temperature, and in a stretched state when above a second temperature.

In a preferred embodiment of the disclosure, the third stretch segment exerts a pressure ranging from 30 mmHg to 200 mmHg on a target lesion.

In a preferred embodiment of the disclosure, the surgical medical device further comprises a rod portion which the support portion extends from.

In a preferred embodiment of the disclosure, the rod portion has a rod end, and the support portion has a first support end, with the rod end being connected to the first support end.

In a preferred embodiment of the disclosure, the support portion comprises a plurality of support conducting wires each having a support spring portion, and the support spring portions provide a tension conducive to maintaining a first stretched volume of the first stretch segment, a second stretched volume of the second stretch segment, and/or a third stretched volume of the third stretch segment when the first stretch segment, the third stretch segment and the second stretch segment are each in a stretched state.

In a preferred embodiment of the disclosure, the rod portion has a rod spring portion providing a tension conducive to maintaining a first stretched volume of the first stretch segment, a second stretched volume of the second stretch segment, and/or a third stretched volume of the third stretch segment when the first stretch segment, the third stretch segment and the second stretch segment are each in a stretched state.

In a preferred embodiment of the disclosure, the control mechanism is a control portion disposed on the rod portion, the control portion connecting to a second support end of the support portion and being movable relative to the rod portion to thereby stretch or contract the first stretch segment, the third stretch segment and the second stretch segment.

In a preferred embodiment of the disclosure, the support portion has a spiral structure, and the control portion rotates relative to the rod portion to thereby stretch or contract the first stretch segment, the third stretch segment and the second stretch segment.

In a preferred embodiment of the disclosure, the support portion is made of a memory alloy, and the control mechanism is in a plastic state when the first stretch segment, the third stretch segment and the second stretch segment are below a first temperature, and in a stretched state when above a second temperature.

In a preferred embodiment of the disclosure, the support portion has a second support end, and the second support end is connected to the rod portion.

In order to achieve the above and other objectives, the disclosure further provides a surgical medical system comprising the surgical medical device of any one of the above embodiments and a containing device having a containing channel. The surgical medical device is at least partially received in the containing channel of the containing device when the surgical medical system is in a ready state.

In a preferred embodiment of the disclosure, the containing device pushes the surgical medical device of the surgical medical system in a first started state out partially to push the first stretch segment of the surgical medical device out of the containing channel, pushes the surgical medical device of the surgical medical system in a second started state out partially to push the third stretch segment of the surgical medical device out of the containing channel, and pushes the surgical medical device of the surgical medical system in a third started state out to push the second stretch segment of the surgical medical device out of the containing channel.

In a preferred embodiment of the disclosure, the containing device has a trigger triggered in a first instance to put the surgical medical system in the first started state, in a second instance to put the surgical medical system in the second started state, and in a third instance to put the surgical medical system in the third started state.

In a preferred embodiment of the disclosure, the containing device has a snap-engaging portion, and the rod portion has a first release portion, a second release portion and a third release portion, wherein the surgical medical system is in the first started state, the second started state or the third started state because of snap-engagement between the snap-engaging portion of the containing device and the first release portion, the second release portion or the third release portion, respectively.

In a preferred embodiment of the disclosure, the surgical medical system further comprises: a cystoscope device connected to the containing device and adapted to obtain a surgical visual field through the containing channel; and an injection device connected to the containing device and adapted to inject a liquid into a surgical lesion through the containing channel.

In a preferred embodiment of the disclosure, the injection device is connected to a regulation device whereby the injection device injects liquids of different temperatures into the surgical lesion.

In a preferred embodiment of the disclosure, the containing device comprises a medical device containing portion demountably mounted at an end of the containing device, and the surgical medical device is at least partially received in the medical device containing portion when the surgical medical system is in the ready state.

In a preferred embodiment of the disclosure, a lateral communication outlet is disposed at a top of the medical device containing portion.

The aforesaid aspects and other aspects of the disclosure are illustrated by non-restrictive, specific embodiments, depicted by accompanying drawings, and described below.

DETAILED DESCRIPTION OF THE EMBODIMENTS

Figure 1:
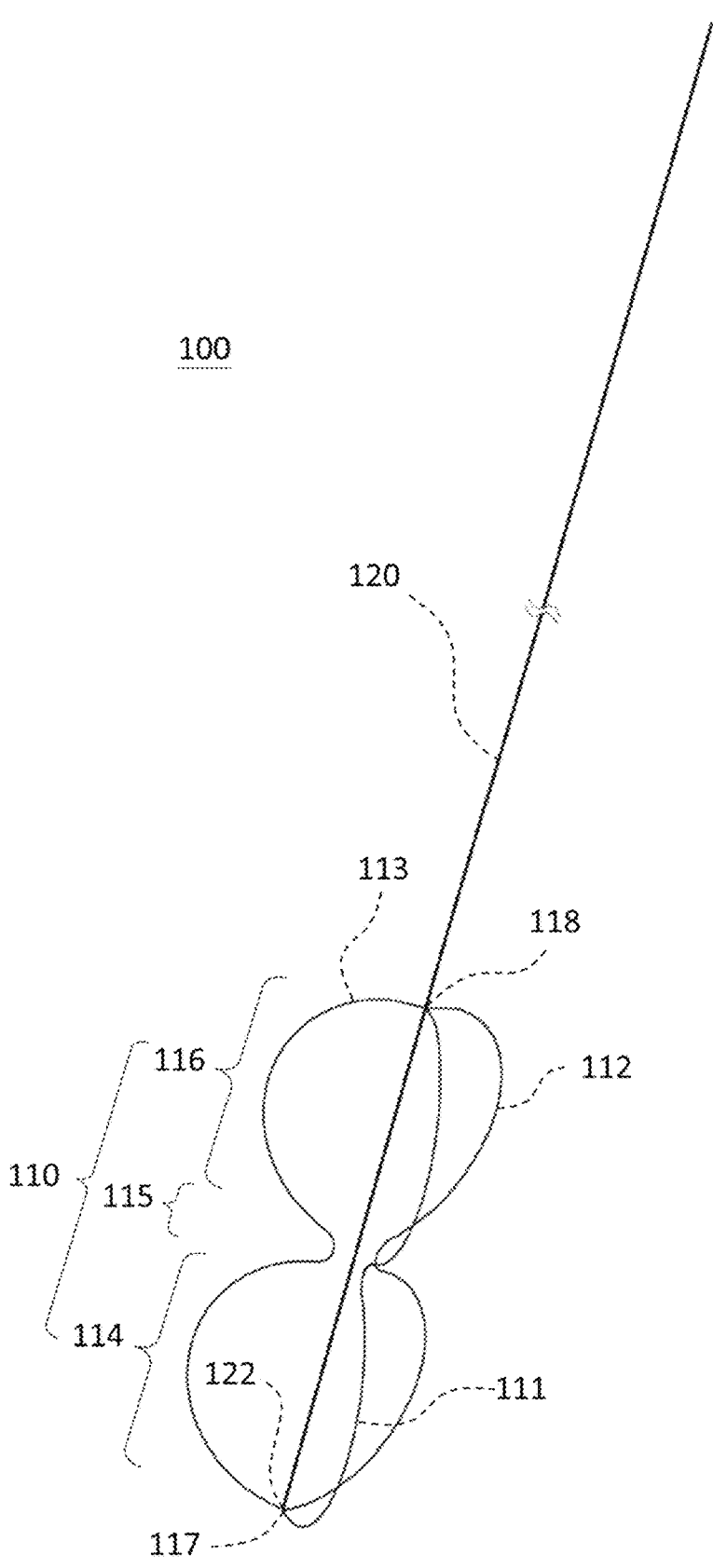
FIG. 1 is a schematic view of a surgical medical device according to a specific embodiment of the disclosure.

Referring to FIG. 1, there is shown a schematic view of a surgical medical device according to a specific embodiment of the disclosure. In the embodiment illustrated by FIG. 1, a surgical medical device 100 comprises a support portion 110 and a rod portion 120. The support portion 110 extends from the rod portion 120. The support portion 110 has a first stretch segment 114, third stretch segment 115 and second stretch segment 116. The third stretch segment 115 is disposed between the first stretch segment 114 and second stretch segment 116. The surgical medical device 100 has a control mechanism. The surgical medical device 100 stretches or contracts the first stretch segment 114, third stretch segment 115 and second stretch segment 116 by the control mechanism. Preferably, when the first stretch segment 114, third stretch segment 115 and second stretch segment 116 are each in a stretched state, the first stretch segment 114 is of a larger stretched volume than the third stretch segment 115, and the second stretch segment 116 is of a larger stretched volume than the third stretch segment 115. In a specific embodiment, the support portion 110 is made of a memory alloy. The control mechanism of the surgical medical device 100 is in a plastic state when the first stretch segment 114, third stretch segment 115 and second stretch segment 116 are below a first temperature, and in a stretched state when above a second temperature. When the first stretch segment 114, third stretch segment 115 and second stretch segment 116 are in a plastic state and are subjected to a compressing external force, the stretched volume of the first stretch segment 114, the stretched volume of the third stretch segment 115, and the stretched volume of the second stretch segment 116 decrease. In a specific embodiment, the first temperature is 20 degrees, and the second temperature is 35 degrees. In different specific embodiments, the first temperature and second temperature are set to any other temperatures as needed. In different specific embodiments, the temperatures of the first stretch segment 114, third stretch segment 115 and second stretch segment 116 are controlled by liquid contact or charging; but the disclosure is not limited thereto.

In the embodiment illustrated by FIG. 1, the support portion 110 comprises support conducting wires 111, 112, 113. The support portion does not necessarily have three support conducting wires; instead, the support conducting wires may be in any number other than three as needed. For example, the support portion may comprise two or four support conducting wires as needed; but the disclosure is not limited thereto. In the embodiment illustrated by FIG. 1, the rod portion 120 has a rod end 122, and the support portion has a first support end 117. The rod end 122 and the first support end 117 are connected. The support portion further has a second support end 118 connected to the rod portion 120. In a specific embodiment, the first support end 117 is an arcuate-shaped arcuate end for preventing the insertion of the first stretch segment 114 into the human body from causing injuries, such as perforation, to the human body. In different specific embodiments, the first stretch segment 114, third stretch segment 115 and second stretch segment 116 of the support portion 110 are of different lengths as needed, allowing the urologist to determine before surgery what size of the applicable surgical medical device is appropriate according to medical images. The stretched volume ratio of the first stretch segment 114, third stretch segment 115 and second stretch segment 116 to each other in this embodiment serves exemplary purposes and can be adjusted or set as needed. For example, the stretched volume of the third stretch segment 115 and the stretched volume of the first stretch segment 114 can be larger than how they look in FIG. 1; but the disclosure is not limited thereto. The first stretch segment 114 and/or second stretch segment 116 in a stretched state take on a specific shape (for example, arcuate shape, round shape, and elliptic shape, but the disclosure is not limited thereto).

Figure 2:
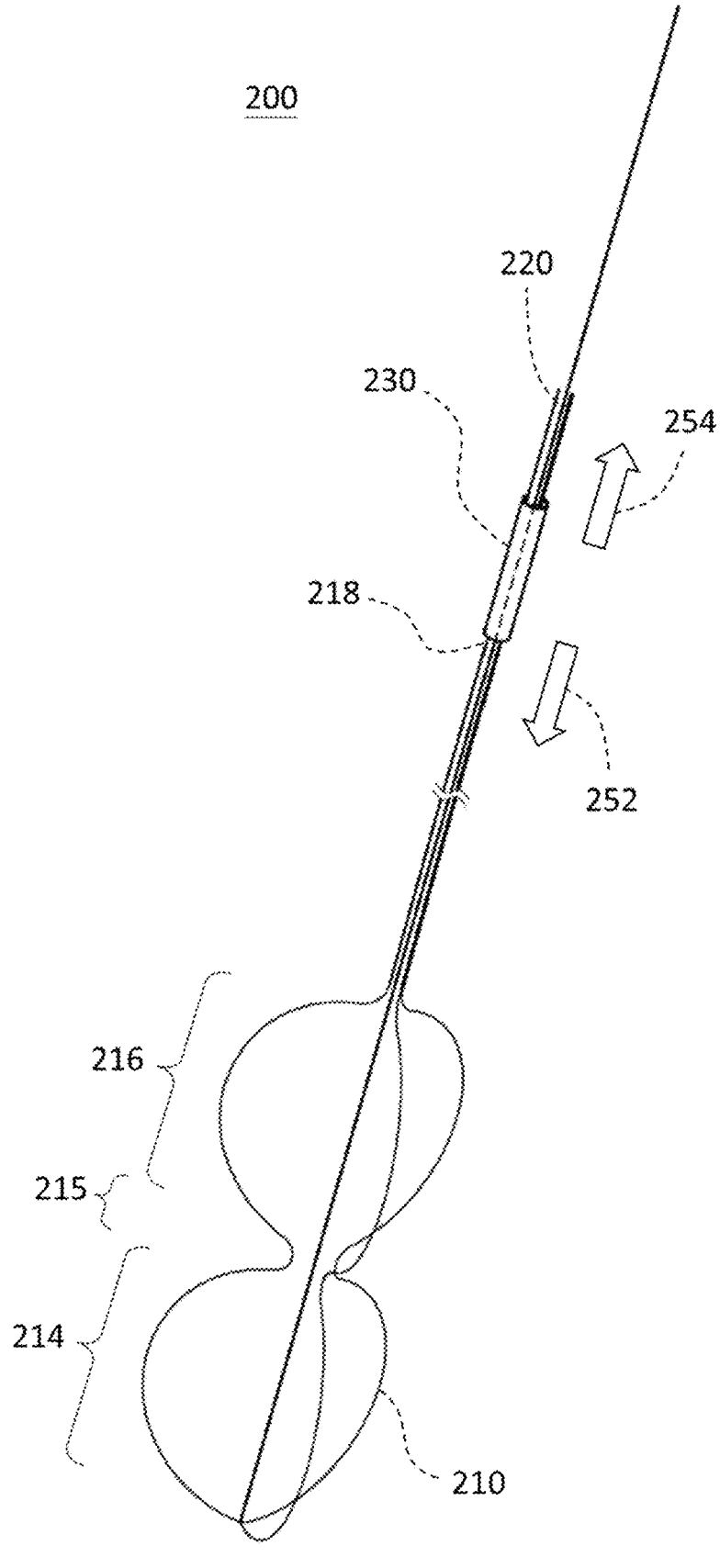
FIG. 2 is a schematic view of the surgical medical device according to a specific embodiment of the disclosure.

Referring to FIG. 2, there is shown a schematic view of the surgical medical device according to a specific embodiment of the disclosure. In the embodiment illustrated by FIG. 2, a surgical medical device 200 comprises a support portion 210, rod portion 220, and control portion 230 movable relative to rod portion 220. A control mechanism of the surgical medical device 200 is the control portion 230 disposed on the rod portion 220. The support portion 210 has a second support end 218. The control portion 230 is connected to the second support end 218. The control portion 230 moves relative to the rod portion 220 to thereby stretch or contract a first stretch segment 214 of the support portion 210, a third stretch segment 215 of the support portion 210, and a second stretch segment 216 of the support portion 210. For example, the control portion 230 moves in the direction 252 relative to the rod portion 220 to thereby stretch the first stretch segment 214, third stretch segment 215 and second stretch segment 216. Alternatively, the control portion 230 moves relative to the rod portion 220 in the direction 254 to thereby contract the first stretch segment 214, third stretch segment 215 and second stretch segment 216. Preferably, when the first stretch segment 214, third stretch segment 215 and second stretch segment 216 are each in a stretched state, the first stretch segment 214 is of a larger stretched volume than the third stretch segment 215, and the second stretch segment 216 is of a larger stretched volume than the third stretch segment 215. In a specific embodiment, the support portion 210 has flexibleness, and thus the first stretch segment 214 and second stretch segment 216 of the support portion 210 stretch or contract when the control portion 230 moves relative to the rod portion 220. The rod portion 220 also has flexibleness in order not to in injure the patient. In different specific embodiments, the support portion 210 has flexibleness, but the rod portion 220 has few or even no flexibleness. Thus, it is easy to control the control portion 230 to move relative to the rod portion 220. In a specific embodiment, the support portion 210 has greater flexibleness than the rod portion 220.

Figure 3:
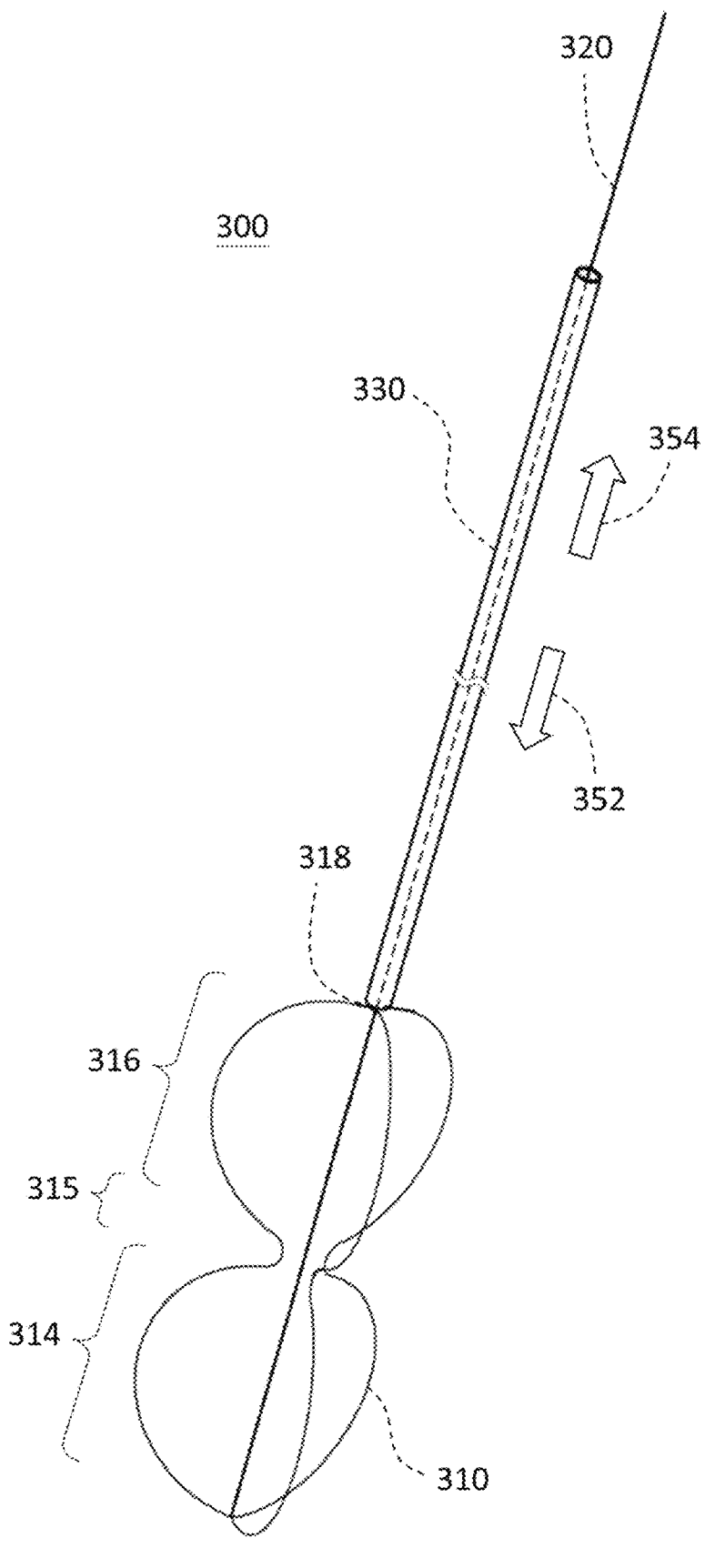
FIG. 3 is a schematic view of the surgical medical device according to a specific embodiment of the disclosure.

Referring to FIG. 3, there is shown a schematic view of the surgical medical device according to a specific embodiment of the disclosure. In the embodiment illustrated by FIG. 3, a surgical medical device 300 comprises a support portion 310, rod portion 320, and control portion 330 movable relative to rod portion 320. The control mechanism of the surgical medical device 300 is the control portion 330 disposed on the rod portion 320. The support portion 310 has a second support end 318. The control portion 330 is separably connected to the second support end 318. (Thus, the control portion 330 is in contact with the second support end 318.) In so doing, the control portion 330 can be easily taken out of the human body. In another specific embodiment, the control portion 330 is inseparably connected to the second support end 318. In the embodiment illustrated by FIG. 3, owing to its movement relative to the rod portion, the control portion 330 can stretch or contract a first stretch segment 314 of the support portion 310, a third stretch segment 315 of the support portion 310, and a second stretch segment 316 of the support portion 310. For example, the control portion 330 pushes the support portion 310 in the direction 352 relative to the rod portion 320 so as to stretch the first stretch segment 314, third stretch segment 315 and second stretch segment 316. Alternatively, the control portion 330 moves in the direction 354 relative to the rod portion 320 to contract the first stretch segment 314, third stretch segment 315 and second stretch segment 316. In a specific embodiment, the second support end 318 is connected to the rod portion 320 while moving relative to the rod portion 320. In a specific embodiment, the support conducting wires of the support portion 310 are fixed to each other by adhesion to form the second support end 318, and an adhesive for use in the adhesion loses its fixation capability above a specific temperature, resulting in separation of the support conducting wires of the support portion 310. Thus, the urologist can heat up the adhesive at any time in whatever way to cause separation of the support conducting wires of the support portion 310, thereby facilitating removal of the surgical medical device 300 from the human body.

Figure 4A:
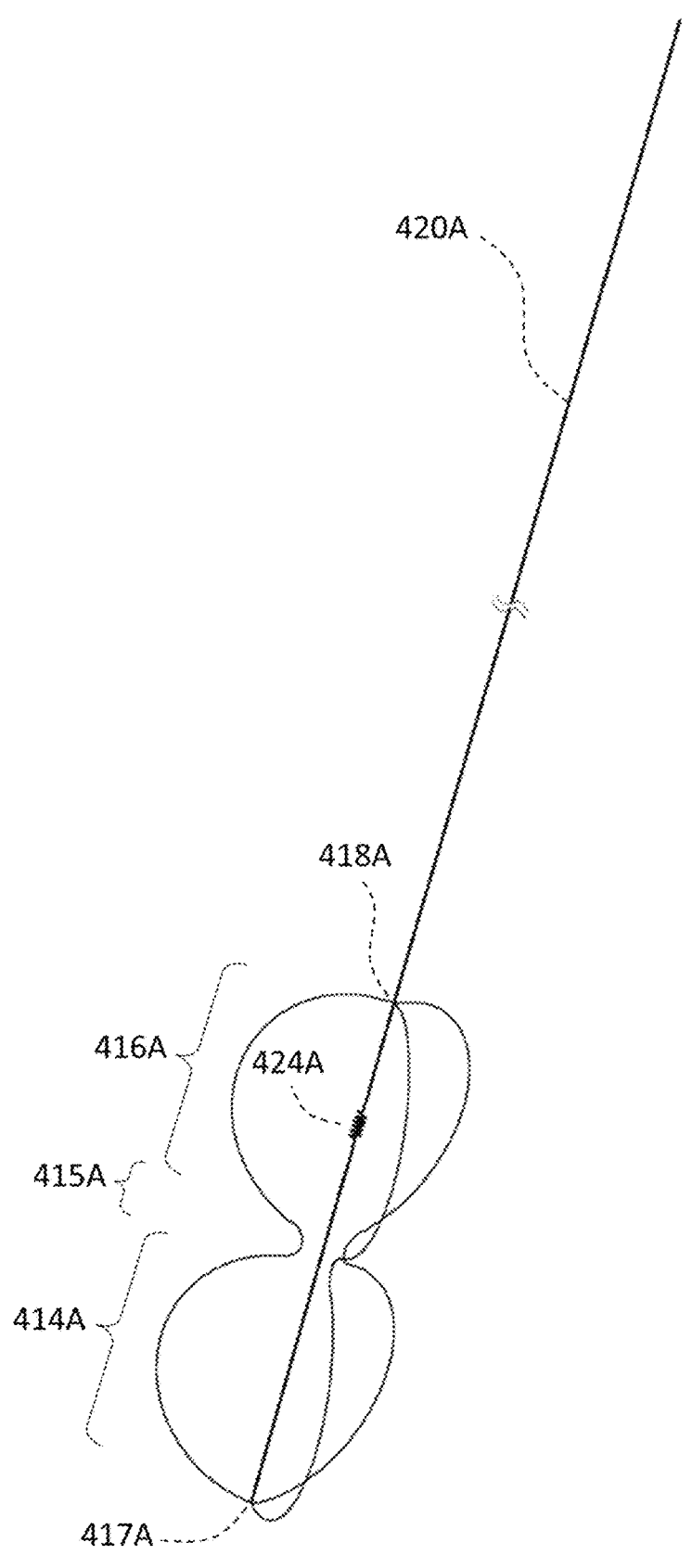
FIG. 4A is a schematic view of the surgical medical device according to a specific embodiment of the disclosure.

Referring to FIG. 4A, there is shown a schematic view of the surgical medical device according to a specific embodiment of the disclosure. In the embodiment illustrated by FIG. 4A, a rod portion 420A has a rod spring portion 424A disposed between a first support end 417A and a second support end 418A. When a first stretch segment 414A, third stretch segment 415A and second stretch segment 416A are each in a stretched state, the rod spring portion 424A provides a tension conducive to maintaining a first stretched volume of the first stretch segment 414A, a second stretched volume of the second stretch segment 416A, and/or a third stretched volume of the third stretch segment 415A. In different specific embodiments, the rod spring portion 424A is disposed at any position between the first support end 417A and the second support end 418A as needed.

Figure 4B:
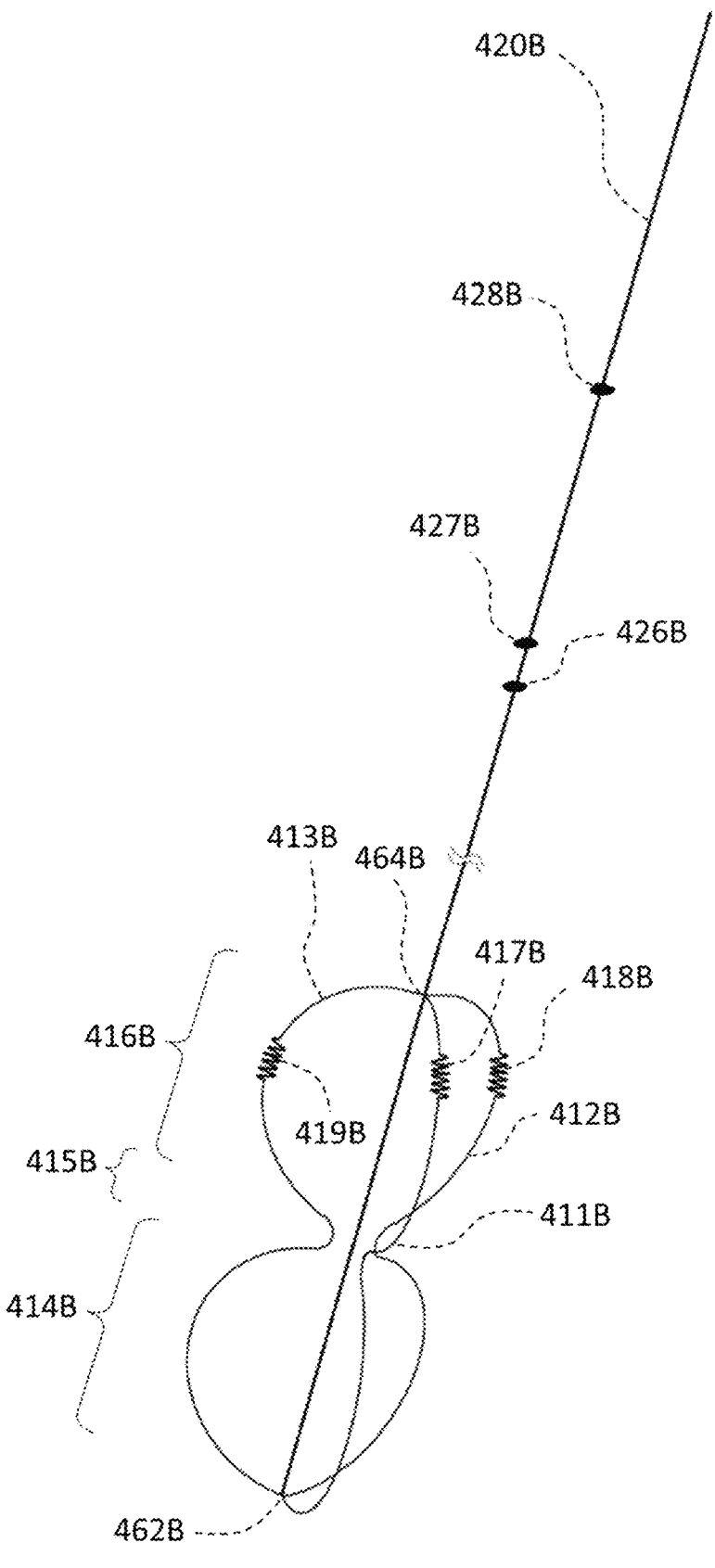
FIG. 4B is a schematic view of the surgical medical device according to a specific embodiment of the disclosure.

Referring to FIG. 4B, there is shown a schematic view of the surgical medical device according to a specific embodiment of the disclosure. In the embodiment illustrated by FIG. 4B, a support conducting wire 411B has a support spring portion 417B, a support conducting wire 412B has a support spring portion 418B, and a support conducting wire 413B has a support spring portion 419B. The support spring portions 417B, 418B, 419B are disposed between a first support end 462B and a second support end 464B. When the first stretch segment 414B, third stretch segment 415B and second stretch segment 416B are each in a stretched state, the support spring portions 417B, 418B, 419B provide a tension conducive to maintaining a first stretched volume of the first stretch segment 414B, a second stretched volume of the second stretch segment 416B, and/or a third stretched volume of the third stretch segment 415B. In different specific embodiments, the support conducting wires 411B, 412B, 413B are discrete support conducting wires or connected support conducting wires. In different specific embodiments, the support spring portions 417B, 418B, 419B are disposed at any position between the first support end 462B and second support end 464B as needed. In the embodiment illustrated by FIG. 4B, a rod portion 420B has a first release portion 426B, second release portion 427B and third release portion 428B. The functions of the first release portion 426B, second release portion 427B and third release portion 428B are described below.

Figure 5:
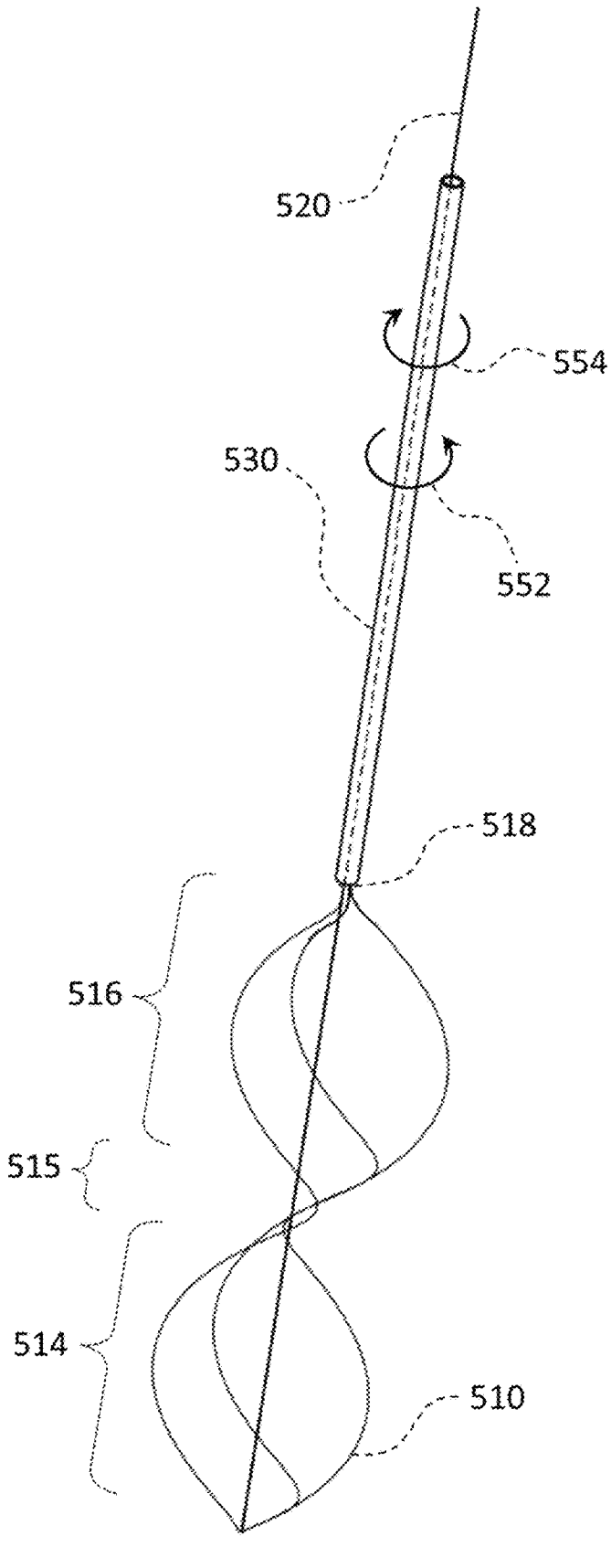
FIG. 5 is a schematic view of the surgical medical device according to a specific embodiment of the disclosure.

Referring to FIG. 5, there is shown a schematic view of the surgical medical device according to a specific embodiment of the disclosure. In the embodiment illustrated by FIG. 5, a second support end 518 of a support portion 510 is connected to a control portion 530. The support portion 510 has a spiral structure. Thus, owing to its rotation relative to a rod portion 520, the control portion 530 can stretch or contract a first stretch segment 514, third stretch segment 515 and second stretch segment 516. For example, the control portion 530 stretches the first stretch segment 514, third stretch segment 515 and second stretch segment 516 in the direction 552 relative to the rod portion 520 or contracts the first stretch segment 514, third stretch segment 515 and second stretch segment 516 in the direction 554 relative to the rod portion 520.

Figure 6:
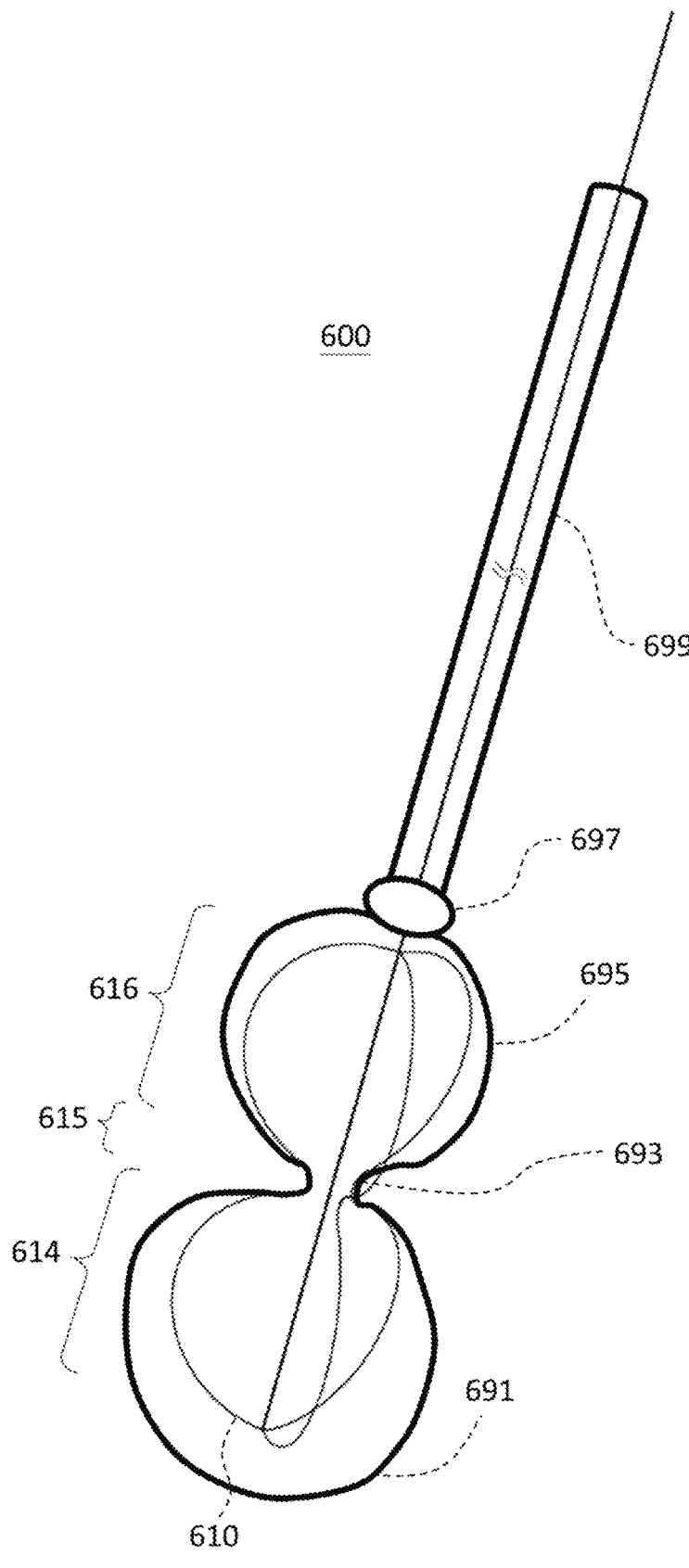
FIG. 6 is a schematic view of the surgical medical device being used in surgery according to a specific embodiment of the disclosure.

Referring to FIG. 6, there is shown a schematic view of the surgical medical device being used in surgery according to a specific embodiment of the disclosure. In the embodiment illustrated by FIG. 6, when a first stretch segment 614, third stretch segment 615 and second stretch segment 616 of a support portion 610 is in a contracted state, a surgical medical device 600 is admitted into the human body via a urethra 699. Once the surgical medical device 600 arrives at its destination, the first stretch segment 614, third stretch segment 615 and second stretch segment 616 stretch. At this point in time, the first stretch segment 614 is disposed in a bladder 691, the third stretch segment 615 at a bladder neck 693, and the second stretch segment 616 in a prostate 695. Thus, during the time period in which the surgical medical device 600 is placed inside the human body, the third stretch segment 615 gradually stretches (or partially cuts) the bladder neck 693, and thus the diameter of the bladder neck 693 increases. In the embodiment illustrated by FIG. 6, when the first stretch segment 614, third stretch segment 615 and second stretch segment 616 are each in a stretched state, the first stretch segment 614 is of a larger stretched volume than the third stretch segment 615, and the second stretch segment 616 is of a larger stretched volume than the third stretch segment 615. Thus, during the time period in which the surgical medical device 600 is placed inside the human body, when the support portion 610 slides toward the urethra 699 or is subjected to a force applied in the direction toward the urethra 699, the first stretch segment 614 inside the bladder 691 presses against the bladder 691 to thereby prevent the second stretch segment 616 from coming into contact with a sphincter 697 to stretch it. When the support portion 610 slides toward the bladder 691 or is subjected to a force applied in the direction toward the bladder 691, the second stretch segment 616 inside the prostate 695 presses against the prostate 695 to thereby prevent the support portion 610 from sliding toward the bladder 691 to a wrong position. FIG. 6 only serves illustrative purposes; during surgery, the bladder neck may have a larger or smaller diameter, and the bladder or prostate may be bigger or smaller in size. The urologist can choose surgical medical devices of different sizes according to the diameter of the bladder neck, the length of the bladder neck, the size of the bladder, and/or the size of the prostate.

In a specific embodiment, the third stretch segment 615 exerts a pressure ranging from 30 mmHg (millimeter of mercury) to 200 mmHg on the bladder neck 693, and thus blood vessels (for example, capillaries) at the bladder neck 693 are compressed, thereby allowing the bladder neck 693 to be stretched (or partially cut) gradually. In different specific embodiments, the pressure which the third stretch segment 615 exerts on the bladder neck 693 is substantially equal to 30 mmHg, 50 mmHg, or 100 mmHg; but the disclosure is not limited thereto. In a specific embodiment, the support portion 610 of the surgical medical device 600 is configured to have flexibleness, and thus the pressure exerted by the third stretch segment 615 of the support portion 610 on a target lesion (for example, the bladder neck) does not exceed a predetermined pressure threshold; the pressure threshold may be set to any level as needed, for example, 30 mmHg or 200 mmHg, but the disclosure is not limited thereto.

Figure 7:
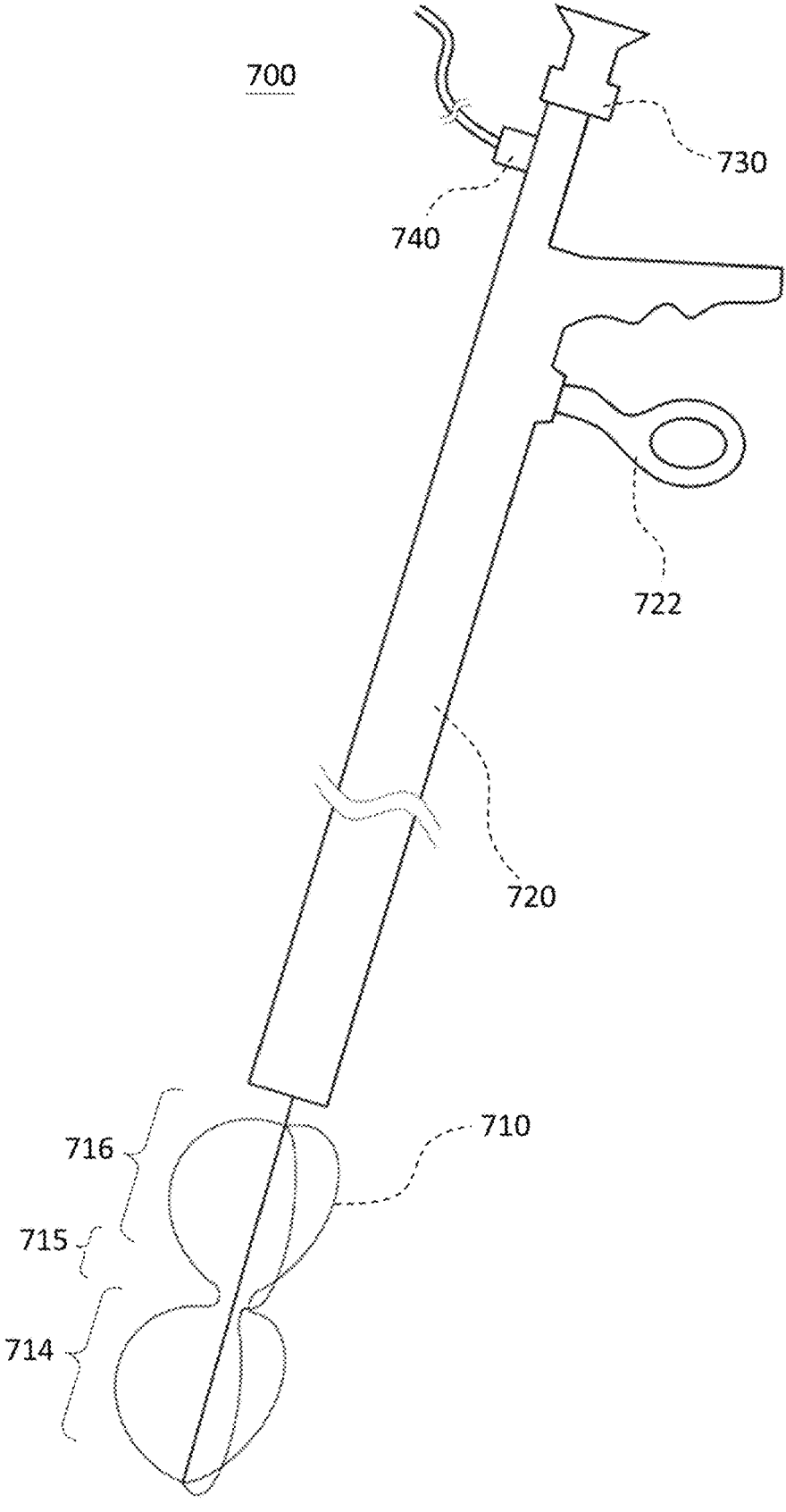
FIG. 7 is a schematic view of a surgical medical system according to a specific embodiment of the disclosure.

Referring to FIG. 7, there is shown a schematic view of a surgical medical system according to a specific embodiment of the disclosure. In the embodiment illustrated by FIG. 7, a surgical medical system 700 comprises a surgical medical device 710, containing device 720, cystoscope device 730 and injection device 740. The containing device 720 has a containing channel for receiving the surgical medical device 710. The cystoscope device 730 connects to the containing device 720. The cystoscope device 730 obtains a surgical visual field through the containing channel. The injection device 740 connects to the containing device 720. The injection device 740 injects a liquid into a surgical lesion through the containing channel. When the surgical medical system 700 is in a ready state, the surgical medical device 710 is at least partially received in the containing channel of the containing device 720. The containing device has a trigger 722. When the trigger 722 is triggered, the surgical medical device 710 is at least partially pushed out of the containing channel. In a specific embodiment, a support portion of the surgical medical device 710 is made of a memory alloy. A first stretch segment 714, third stretch segment 715 and second stretch segment 716 of the surgical medical device 710 are in a plastic state when below a first temperature, and in a stretched state when above a second temperature. The injection device 740 connects to a regulation device. The injection device 740 injects liquids of different temperatures into a surgical lesion through the regulation device. Thus, the injection of the liquids of different temperatures enables the first stretch segment 714, third stretch segment 715 and second stretch segment 716 to be in a plastic state or a stretched state.

Figure 8A:
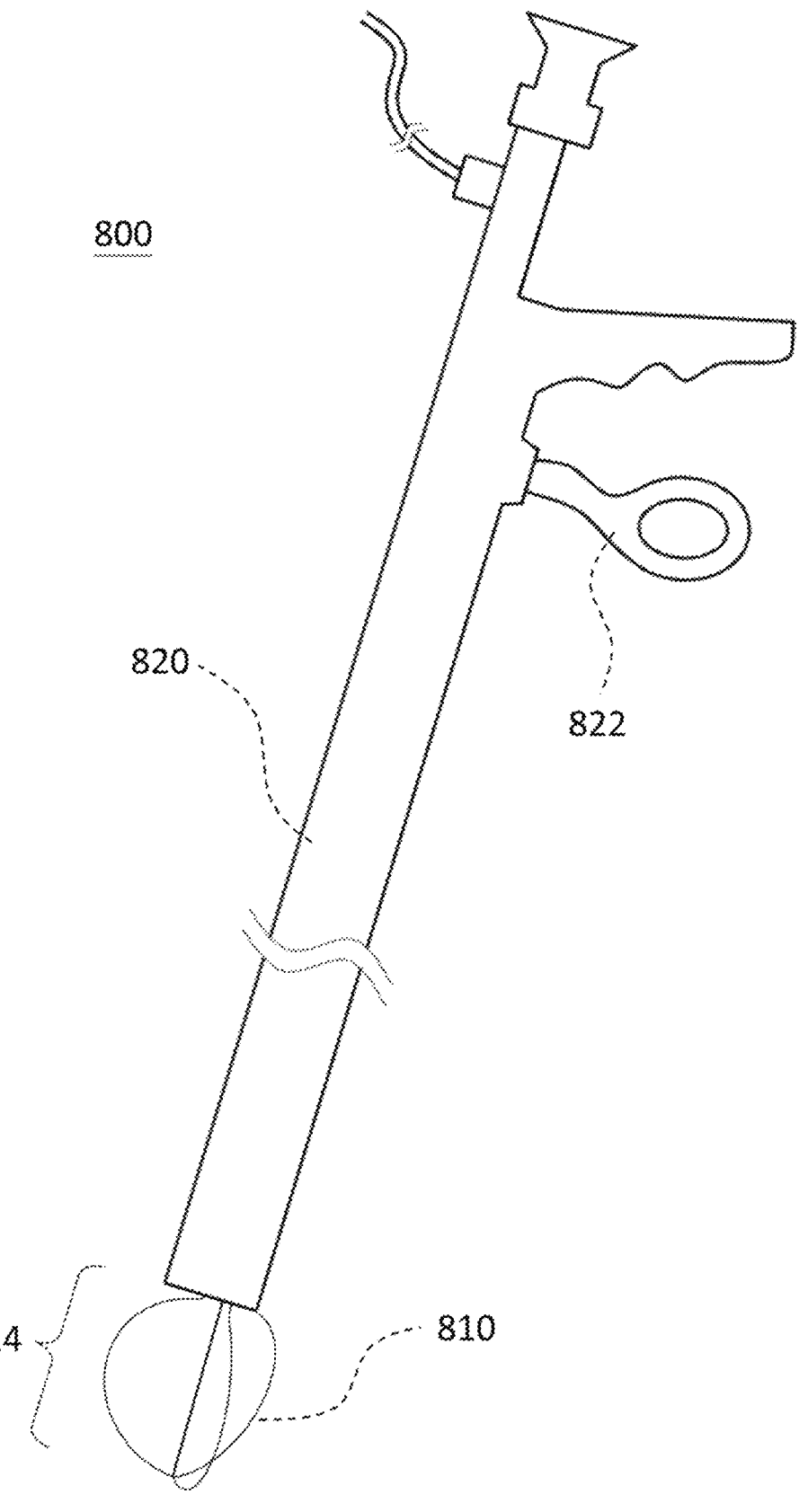
FIG. 8A is a schematic view of the surgical medical system according to a specific embodiment of the disclosure.
Figure 8B:
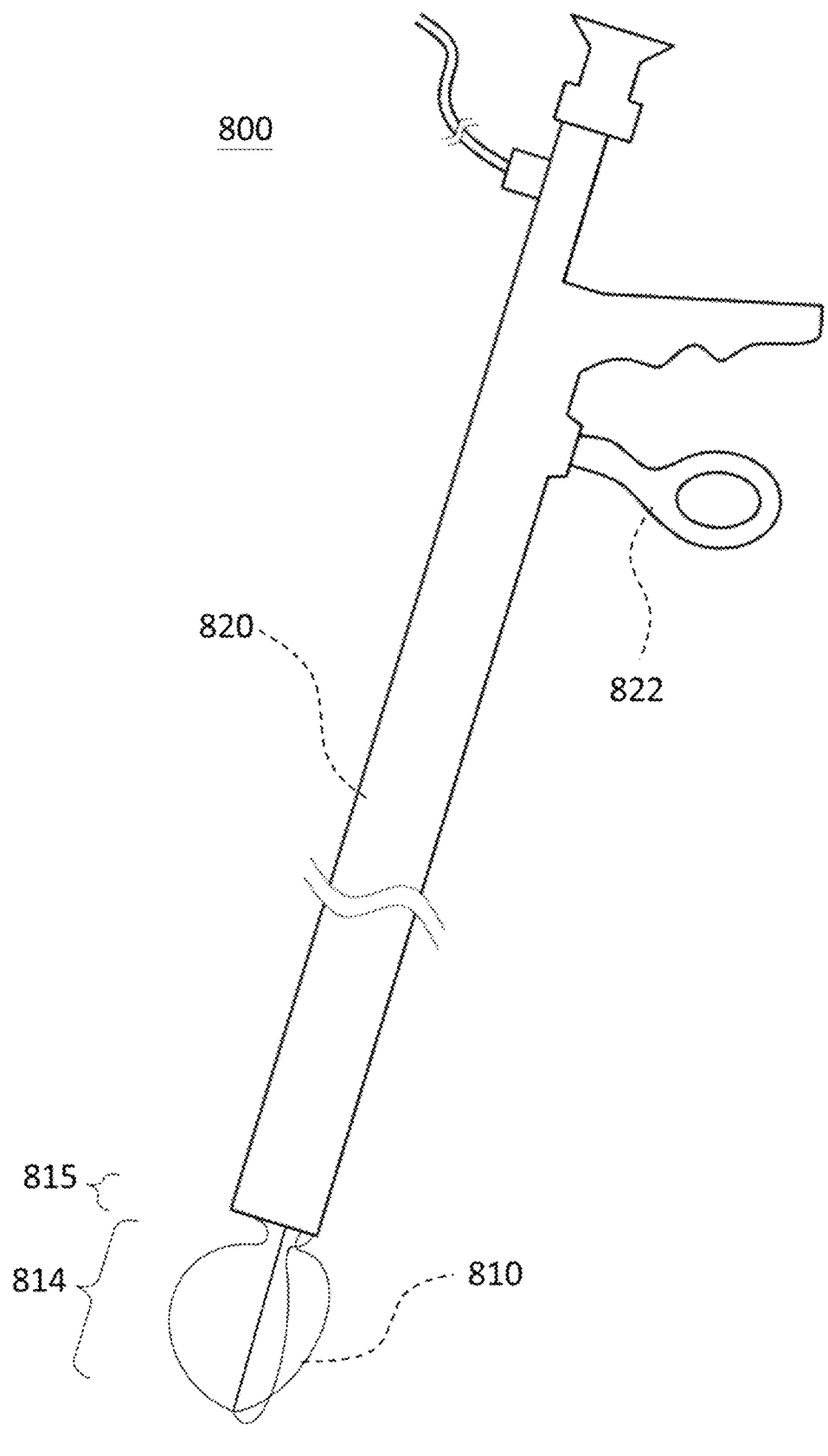
FIG. 8B is a schematic view of the surgical medical system according to a specific embodiment of the disclosure.
Figure 8C:
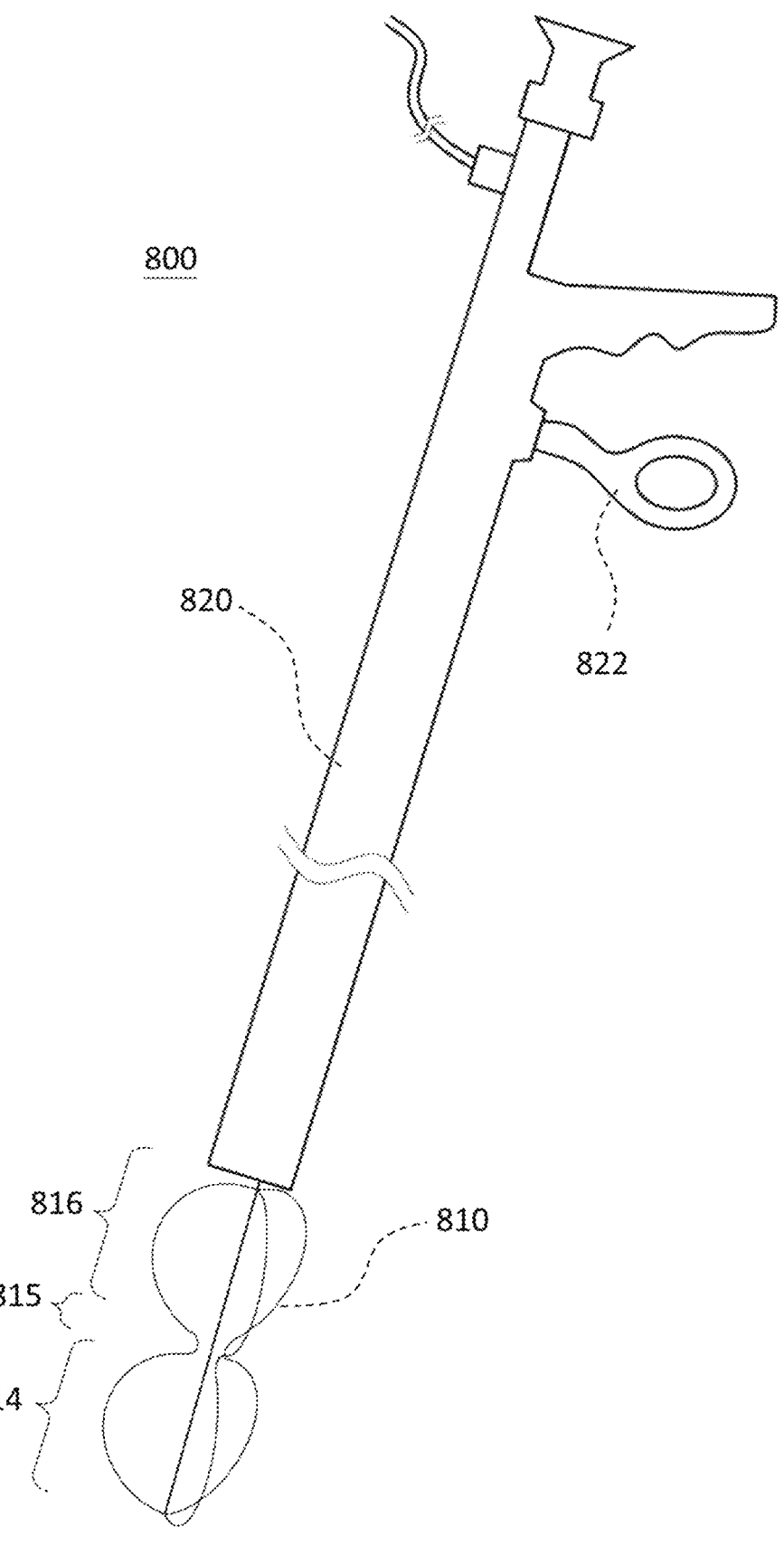
FIG. 8C is a schematic view of the surgical medical system according to a specific embodiment of the disclosure.

Referring to FIG. 8A through FIG. 8C, there are shown schematic views of the surgical medical system according to a specific embodiment of the disclosure. In the embodiment illustrated by FIG. 8A through FIG. 8C, a containing device 820 has a three-stage triggering mechanism. When a trigger 822 is triggered in the first instance (see FIG. 8A), a surgical medical system 800 is in a first started state; thus, the containing device 820 pushes a surgical medical device 810 out partially, and in consequence a first stretch segment 814 of the surgical medical device 810 is pushed out of the containing channel. When the trigger 822 is triggered in the second instance (see FIG. 8B), the surgical medical system 800 is in a second started state; thus, the containing device 820 pushes the surgical medical device 810 out partially, and in consequence a third stretch segment 815 of the surgical medical device 810 is pushed out of the containing channel. When the trigger 822 is triggered in the third instance (see FIG. 8C), the surgical medical system 800 is in a third started state; thus, the containing device 820 pushes the surgical medical device 810 out, and in consequence a second stretch segment 816 of the surgical medical device 810 is pushed out of the containing channel. In a specific embodiment, the containing device 820 has a snap-engaging portion in the containing channel and is snap-engaged with a first release portion, second release portion or third release portion of the surgical medical device 810 through the snap-engaging portion, thereby allowing the surgical medical system 800 to be in a first started state, second started state or third started state, respectively. The first release portion, second release portion and third release portion are arranged in a way, for example, shown in FIG. 4B (see the first release portion 426B, second release portion 427B and third release portion 428B shown in FIG. 4B).

Figure 9:
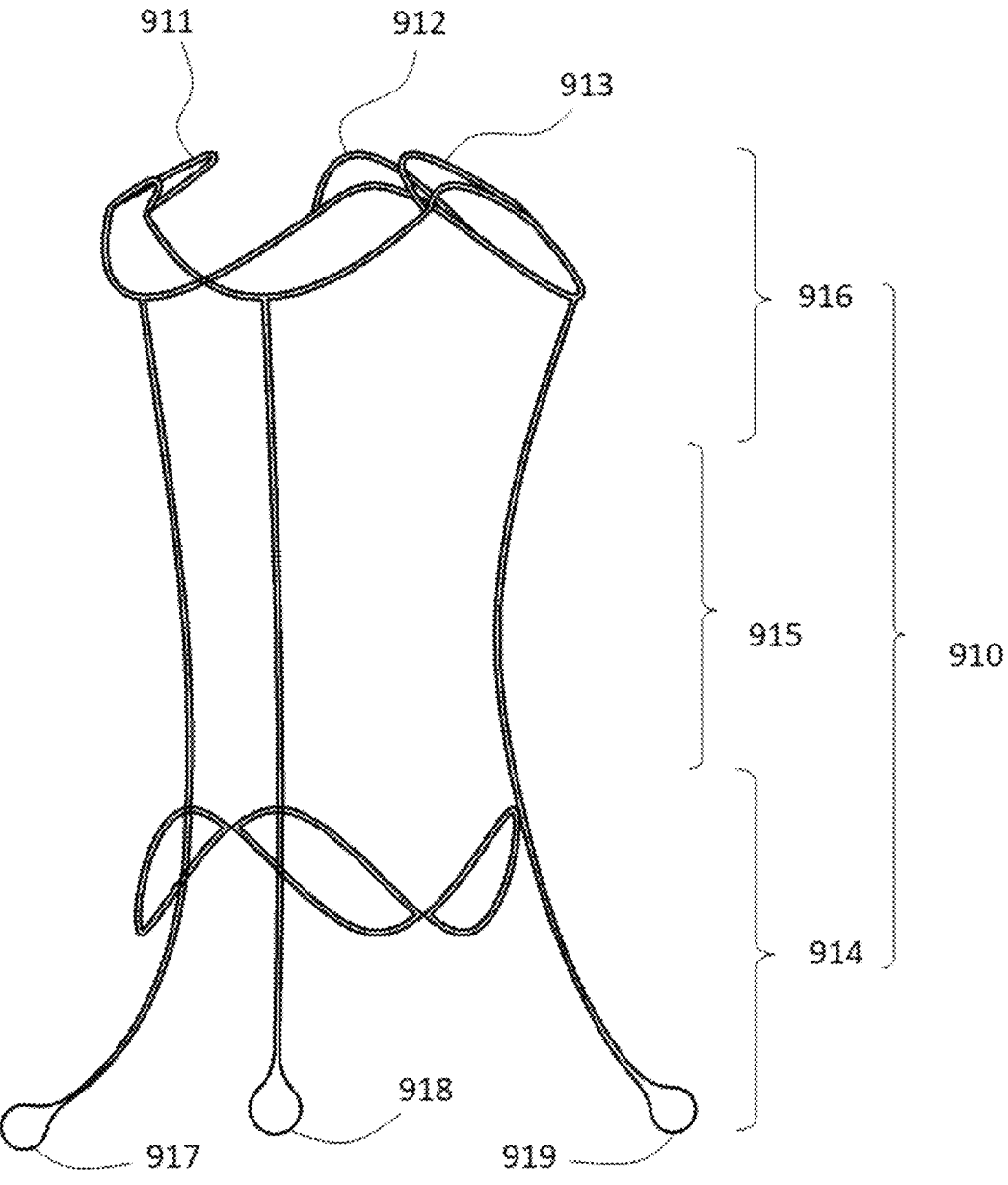
FIG. 9 is a schematic view of the surgical medical device according to a specific embodiment of the disclosure.

Referring to FIG. 9, there is shown a schematic view of the surgical medical device according to a specific embodiment of the disclosure. In the embodiment illustrated by FIG. 9, a surgical medical device 900 comprises a support portion 910. The support portion 910 has a first stretch segment 914, third stretch segment 915 and second stretch segment 916. The third stretch segment 915 is disposed between the first stretch segment 914 and second stretch segment 916. The surgical medical device 900 has a control mechanism. The surgical medical device 900 stretches or contracts the first stretch segment 914, third stretch segment 915 and second stretch segment 916 by the control mechanism. Preferably, when the first stretch segment 914, third stretch segment 915 and second stretch segment 916 are each in a stretched state, the first stretch segment 914 is of a larger stretched volume than the third stretch segment 915, and the second stretch segment 916 is of a larger stretched volume than the third stretch segment 915. Preferably, the first stretch segment 914 has arcuate ends 917, 918, 919 for preventing the insertion of the first stretch segment 914 into the human body from causing injuries, such as perforation, to the human body. Preferably, the second stretch segment 916 has folding auxiliary portions 911, 912, 913 which, coupled with a folding device, are effective in folding and removing the surgical medical device 900 out of the human body. The folding auxiliary portions 911, 912, 913 are described in detail later. Alternatively, the support portion 910 comprises one support conducting wire as needed or comprises a plurality of support conducting wires as needed. At least two of the ends 917, 918, 919 of the first stretch segment 914 are in communication with each other to thereby take on a specific shape (for example, the arcuate shape of the first stretch segment 114 in FIG. 1). The at least two ends 917, 918, 919 in communication with each other are not necessarily in arcuate shape but may be in any other shapes as needed.

In a specific embodiment, when the surgical medical device 900 is placed in the human body, the first stretch segment 914 is disposed in the bladder, the third stretch segment 915 at the bladder neck, and the second stretch segment 916 in the prostate. Thus, during the time period in which the surgical medical device 900 is placed inside the human body, the third stretch segment 915 gradually stretches (or partially cuts) the bladder neck, and thus the diameter of the bladder neck increases. Thus, during the time period in which the surgical medical device 900 is placed in the human body, when the support portion 910 slides toward the urethra or is subjected to a force applied in the direction toward the urethra, the first stretch segment 914 in the bladder presses against the bladder to thereby prevent the second stretch segment 916 from coming into contact with the sphincter to stretch it. When the support portion 910 slides toward the bladder or is subjected to a force applied in the direction toward the bladder, the second stretch segment 916 inside the prostate presses against the prostate to thereby prevent the support portion 910 from sliding toward the bladder to a wrong position. FIG. 9 only serves illustrative purposes; the stretched volumes of the first stretch segment 914, third stretch segment 915, and second stretch segment 916 may be larger or smaller as needed; for example, the stretched volumes of the first stretch segment 914 and second stretch segment 916 may be larger, or the stretched volume of the third stretch segment 915 may be smaller.

In a specific embodiment, the third stretch segment 915 exerts a pressure ranging from 30 mmHg to 200 mmHg on the bladder neck, and thus blood vessels (for example, capillaries) at the bladder neck are compressed, thereby allowing the bladder neck to be stretched (or partially cut) gradually. In different specific embodiments, the pressure which the third stretch segment 915 exerts on the bladder neck is substantially equal to 30 mmHg, 50 mmHg, or 100 mmHg; but the disclosure is not limited thereto.

In a specific embodiment, the support portion 910 is made of a memory alloy. The control mechanism of the surgical medical device 900 is in a plastic state when the first stretch segment 914, third stretch segment 915 and second stretch segment 916 are below a first temperature, and in a stretched state when above a second temperature. When the first stretch segment 914, third stretch segment 915 and second stretch segment 916 are in a plastic state and are subjected to a compressing external force, the stretched volume of the first stretch segment 914, the stretched volume of the third stretch segment 915, and the stretched volume of the second stretch segment 916 decrease. In a specific embodiment, the first temperature is 20 degrees, and the second temperature is 35 degrees. In different specific embodiments, the first temperature and second temperature are set to any other temperatures as needed. In different specific embodiments, the temperatures of the first stretch segment 914, third stretch segment 915 and second stretch segment 916 are controlled by liquid contact or charging; but the disclosure is not limited thereto.

Figure 10:
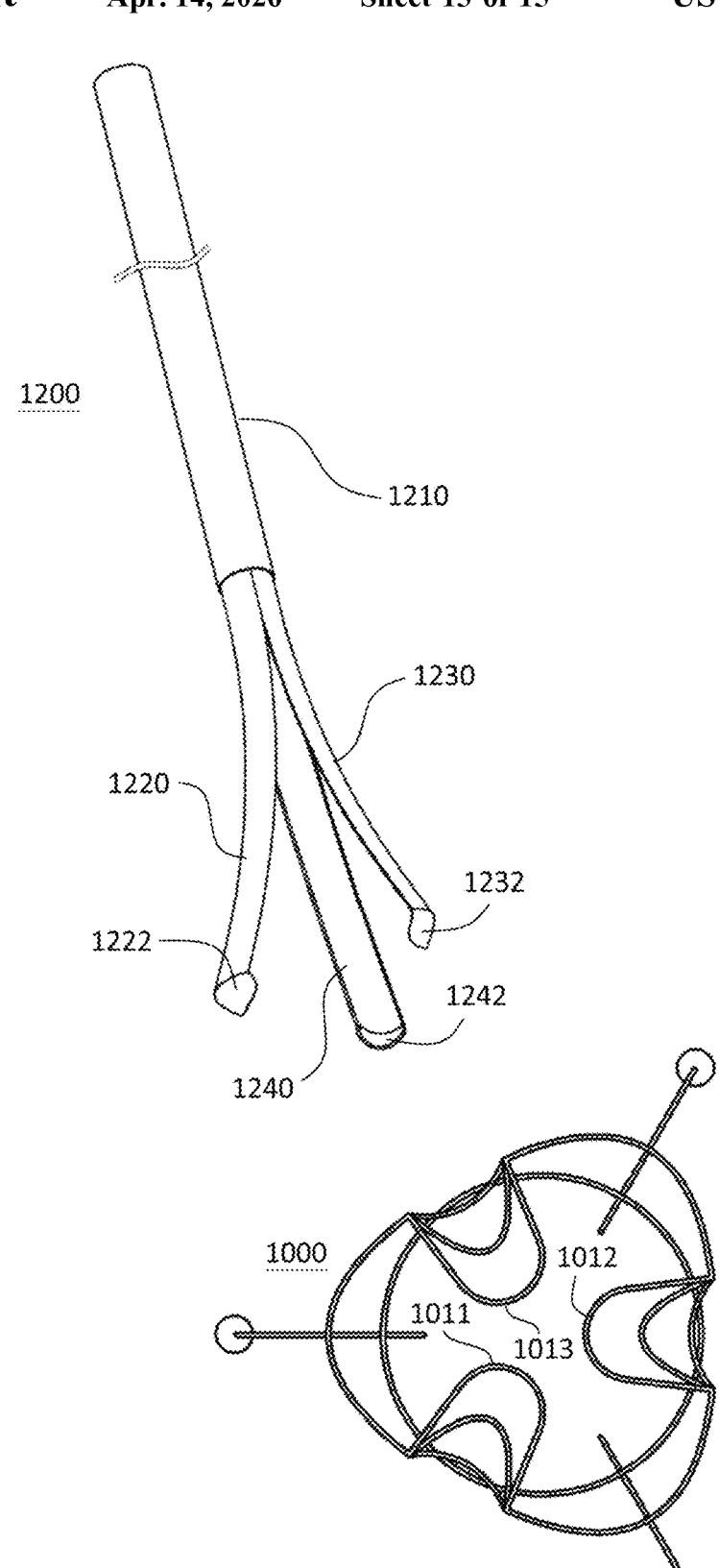
FIG. 10 is a schematic view of a folding device for folding the surgical medical device according to a specific embodiment of the disclosure.

Referring to FIG. 10, there is shown a schematic view of a folding device for folding the surgical medical device according to a specific embodiment of the disclosure. In the embodiment illustrated by FIG. 10, folding auxiliary portions 1011, 1012, 1013 are disposed at the second stretch segment of a surgical medical device 1000. A folding device 1200 comprises a tubular portion 1210 and a plurality of folding supports 1220, 1230, 1240. The respective ends of the folding supports 1220, 1230, 1240 have engaging ends 1222, 1232, 1242, respectively. The folding supports 1220, 1230, 1240 may be admitted into the tubular portion 1210 or at least partially protruded from the tubular portion 1210.

The process of folding the surgical medical device 1000 into the tubular portion 1210 entails inserting the folding device 1200 into the human body via the urethra until the folding device 1200 reaches its destination, protruding the folding supports 1220, 1230, 1240 from the tubular portion 1210, allowing the engaging ends 1222, 1232, 1242 of the folding supports 1220, 1230, 1240 to engage with the folding auxiliary portions 1011, 1012, 1013 of the surgical medical device 1000 inside the human body, respectively, and moving the folding supports 1220, 1230, 1240 along and into the tubular portion 1210. The surgical medical device 1000 is folded into the tubular portion 1210, not only because the engaging ends 1222, 1232, 1242 are engaged with the folding auxiliary portions 1011, 1012, 1013, respectively, but also because the folding supports 1220, 1230, 1240 are admitted into the tubular portion 1210. In a specific embodiment, after the engaging ends 1222, 1232, 1242 have been engaged with the folding auxiliary portions 1011, 1012, 1013, respectively, it is feasible to directly pull the folding device 1200 in the direction away from the human body in order to remove the surgical medical device 1000 from the human body without first folding the surgical medical device 1000 into the tubular portion 1210 of the folding device 1200.

Figure 11A:
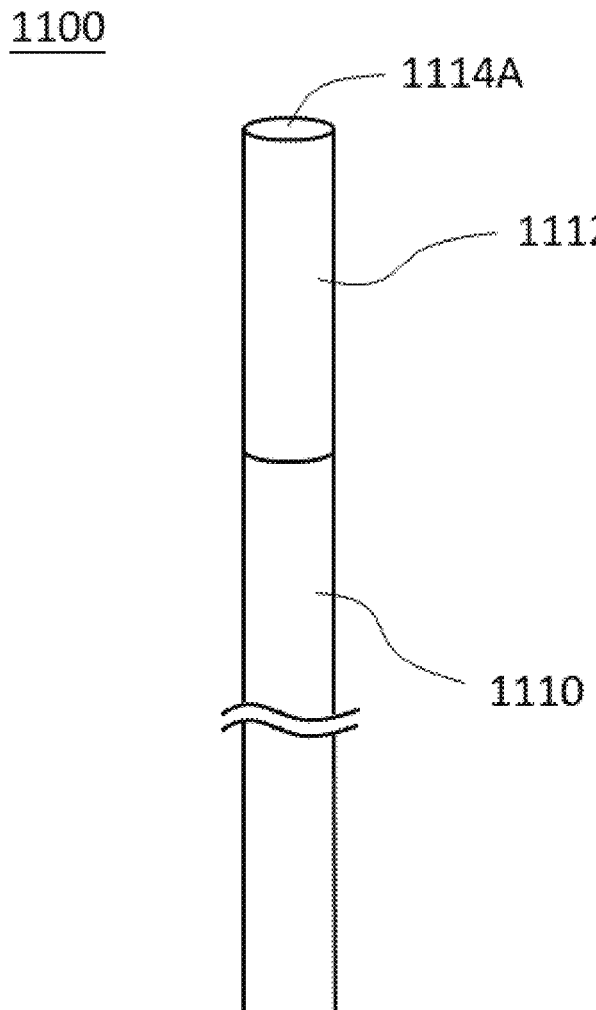
FIG. 11A is a schematic view of the surgical medical system according to a specific embodiment of the disclosure.

Referring to FIG. 11A, there is shown a schematic view of the surgical medical system according to a specific embodiment of the disclosure. In the embodiment illustrated by FIG. 11A, a surgical medical system 1100 comprises a containing device 1110 and surgical medical device (not shown). The containing device 1110 comprises a medical device containing portion 1112. The surgical medical device is at least partially received in the medical device containing portion. When the surgical medical device is at least partially received in the medical device containing portion, the surgical medical device is in a ready state. Preferably, the medical device containing portion 1112 is demountably mounted at an end of the containing device 1110. Alternatively, the medical device containing portion 1112 is part of the containing device 1110. In a specific embodiment, the surgical medical system 1100 further comprises an endoscope device (for example, cystoscope device) and/or injection device. The endoscope device is connected to the containing device 1110 or disposed in the containing channel of the containing device 1110. The endoscope device obtains a surgical visual field through the containing channel. Preferably, the containing channel of the containing device 1110 and the interior of the medical device containing portion are in communication with each other. The containing channel of the containing device 1110 extends and connects to an outlet 1114A of the medical device containing portion 1112.

Figure 11B:
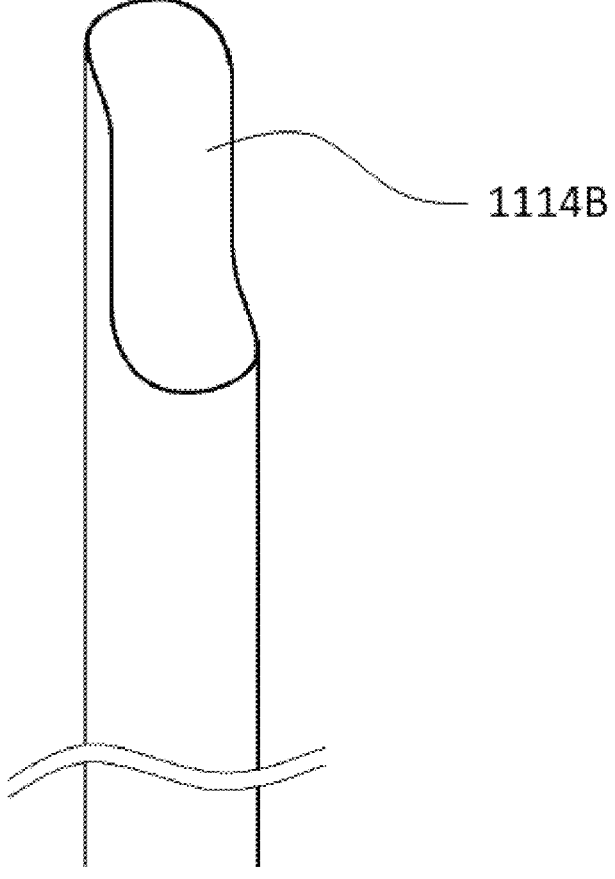
FIG. 11B is a schematic view of a medical device containing portion according to a specific embodiment of the disclosure.

In the embodiment illustrated by FIG. 11A, when the surgical medical device is in a folded state (also known as "contracted state"), the surgical medical device is at least partially placed in the medical device containing portion 1112 (for example, by inserting the surgical medical device into the medical device containing portion 1112 via the outlet 1114A at the top of the medical device containing portion 1112.) For example, when the surgical medical device is in the plastic state, the surgical medical device is compressed and shrunken, and then the surgical medical device is at least partially placed in the medical device containing portion 1112. In a specific embodiment, the outlet of the medical device containing portion is a lateral communication outlet. The lateral communication outlet comprises a top outlet and a lateral outlet which are in communication with each other and is exemplified by a lateral communication outlet 1114B shown in FIG. 11B. The lateral communication outlet prevents unnecessary displacement of the surgical medical device in the course of removal of the medical device containing portion. In the course of its gradual removal from the medical device containing portion and its gradual stretching, the surgical medical device is likely to rapidly slide under a stretching force, via the outlet, out or into the medical device containing portion, and in consequence the surgical medical device is unlikely to be positioned correctly. Thus, in some embodiments, the outlet is a lateral communication outlet in order to prevent the aforesaid unnecessary rapid displacement.

The surgical medical device and system of the disclosure are depicted by drawings and described above. Specific embodiments of the disclosure merely serve illustrative purposes. Various changes made to the specific embodiments without departing from the spirit and claims of the disclosure must be deemed falling within the scope of the claims of the disclosure. Accordingly, the spirit and scope of the disclosure should be defined by the appended claims, and the specific embodiments described herein are not restrictive of the disclosure.

What is claimed is:

1. A surgical medical device, comprising:
    a support portion having a first stretch segment, a second stretch segment, and a third stretch segment disposed between the first stretch segment and the second stretch segment,
    wherein the surgical medical device has a control mechanism, and the surgical medical device stretches or contracts the first stretch segment, the third stretch segment and the second stretch segment by the control mechanism;

wherein the support portion has at least one folding auxiliary portion at the second stretch segment.

2. The surgical medical device of claim 1, wherein the support portion has at least one arcuate end at the first stretch segment.

3. The surgical medical device of claim 1, wherein the support portion comprises a plurality of support conducting wires.

4. The surgical medical device of claim 1, wherein the support portion is made of a memory alloy, and the control mechanism is in a plastic state when the first stretch segment, the third stretch segment and the second stretch segment are below a first temperature, and in a stretched state when above a second temperature.

5. The surgical medical device of claim 1, wherein the third stretch segment exerts a pressure ranging from 30 mmHg to 200 mmHg on a target lesion.

6. The surgical medical device of claim 1, further comprising a rod portion which the support portion extends from.

7. The surgical medical device of claim 6, wherein the rod portion has a rod end, and the support portion has a first support end, with the rod end being connected to the first support end.

8. The surgical medical device of claim 6, wherein the support portion comprises a plurality of support conducting wires each having a support spring portion, and the support spring portions provide a tension conducive to maintaining a first stretched volume of the first stretch segment, a second stretched volume of the second stretch segment, and/or a third stretched volume of the third stretch segment when the first stretch segment, the third stretch segment and the second stretch segment are each in a stretched state.

9. The surgical medical device of claim 6, wherein the rod portion has a rod spring portion providing a tension conducive to maintaining a first stretched volume of the first stretch segment, a second stretched volume of the second stretch segment, and/or a third stretched volume of the third stretch segment when the first stretch segment, the third stretch segment and the second stretch segment are each in a stretched state.

10. The surgical medical device of claim 6, wherein the control mechanism is a control portion disposed on the rod portion, the control portion connecting to a second support end of the support portion and being movable relative to the rod portion to thereby stretch or contract the first stretch segment, the third stretch segment and the second stretch segment.

11. The surgical medical device of claim 10, wherein the support portion has a spiral structure, and the control portion rotates relative to the rod portion to thereby stretch or contract the first stretch segment, the third stretch segment and the second stretch segment.

12. The surgical medical device of claim 6, wherein the support portion is made of a memory alloy, and the control mechanism is in a plastic state when the first stretch segment, the third stretch segment and the second stretch segment are below a first temperature, and in a stretched state when above a second temperature.

13. The surgical medical device of claim 12, wherein the support portion has a second support end, and the second support end is connected to the rod portion.

14. A surgical medical system, comprising:
    a surgical medical device, comprising:

a support portion having a first stretch segment, a second stretch segment, and a third stretch segment disposed between the first stretch segment and the second stretch segment, wherein the surgical medical device has a control mechanism, and the surgical medical device stretches or contracts the first stretch segment, the third stretch segment and the second stretch segment by the control mechanism, wherein the support portion has at least one folding auxiliary portion at the second stretch segment, a containing device having a containing channel, wherein the surgical medical device is at least partially received in the containing channel of the containing device when the surgical medical system is in a ready state.

15. The surgical medical system of claim 14, wherein the containing device pushes the surgical medical device of the surgical medical system in a first started state out partially to push the first stretch segment of the surgical medical device out of the containing channel, pushes the surgical medical device of the surgical medical system in a second started state out partially to push the third stretch segment of the surgical medical device out of the containing channel, and pushes the surgical medical device of the surgical medical system in a third started state out to push the second stretch segment of the surgical medical device out of the containing channel.

16. The surgical medical system of claim 15, wherein the containing device has a trigger triggered in a first instance to put the surgical medical system in the first started state, in a second instance to put the surgical medical system in the second started state, and in a third instance to put the surgical medical system in the third started state.

17. The surgical medical system of claim 14, wherein the containing device has a snap-engaging portion, and the rod portion has a first release portion, a second release portion and a third release portion, wherein the surgical medical system is in the first started state, the second started state or the third started state because of snap-engagement between the snap-engaging portion of the containing device and the first release portion, the second release portion or the third release portion, respectively.

18. The surgical medical system of claim 14, further comprising:

a cystoscope device connected to the containing device and adapted to obtain a surgical visual field through the containing channel; and an injection device connected to the containing device and adapted to inject a liquid into a surgical lesion through the containing channel.

19. The surgical medical system of claim 18, wherein the injection device is connected to a regulation device whereby the injection device injects liquids of different temperatures into the surgical lesion.

20. The surgical medical system of claim 14, wherein the containing device comprises a medical device containing portion demountably mounted at an end of the containing device, and the surgical medical device is at least partially received in the medical device containing portion when the surgical medical system is in the ready state.

21. The surgical medical system of claim 20, wherein a lateral communication outlet is disposed at a top of the medical device containing portion.

* * * * *